United States Patent [19]

Horner et al.

[11] Patent Number: 5,554,172
[45] Date of Patent: Sep. 10, 1996

[54] DIRECTED ENERGY SURGICAL METHOD AND ASSEMBLY

[75] Inventors: Glenn A. Horner; Scott A. Miller; Warren P. Heim; Larry K. Blankenship; James L. Brassell, all of Boulder, Colo.

[73] Assignee: The Larren Corporation, Boulder, Colo.

[21] Appl. No.: 437,321

[22] Filed: May 9, 1995

[51] Int. Cl.⁶ ........................................ A61N 1/08
[52] U.S. Cl. ................ 607/88; 607/104; 607/105; 606/22; 606/34
[58] Field of Search ......................... 607/104, 105, 607/113, 115, 116, 153, 88; 239/337–339; 128/200.14, 200.21; 606/22, 34, 35, 41

[56] References Cited

U.S. PATENT DOCUMENTS

| | | | |
|---|---|---|---|
| 4,060,088 | 11/1977 | Morrison, Jr. et al. | 128/303.17 |
| 4,719,914 | 1/1988 | Johnson | 128/303.1 |
| 4,911,159 | 3/1990 | Johnson et al. | 606/37 |
| 4,929,246 | 5/1990 | Sinofsky | 606/8 |
| 5,092,864 | 3/1992 | Hayes et al. | 606/10 |
| 5,160,334 | 11/1992 | Billings et al. | 606/34 |
| 5,167,659 | 12/1992 | Ohtomo et al. | 606/40 |
| 5,188,532 | 2/1993 | Levy | 433/216 |
| 5,273,524 | 12/1993 | Fox et al. | 604/21 |
| 5,277,696 | 1/1994 | Hagen | 606/49 |
| 5,300,069 | 4/1994 | Hunsberger et al. | 606/37 |
| 5,304,176 | 4/1994 | Phillips | 606/41 |
| 5,306,238 | 4/1994 | Fleenor | 606/42 |
| 5,318,562 | 6/1994 | Levy et al. | 606/16 |
| 5,324,254 | 6/1994 | Phillips | 604/21 |
| 5,334,193 | 8/1994 | Nardella | 606/41 |

FOREIGN PATENT DOCUMENTS 4138468   6/1983   Germany .

*Primary Examiner*—Angela D. Sykes
*Assistant Examiner*—Ryan C. Carter
*Attorney, Agent, or Firm*—Sheridan Ross & McIntosh

[57] ABSTRACT

An improved directed energy surgical method and assembly is disclosed. The method and assembly contemplate the application of a directed energy stream to tissue and the application of a liquid mist stream to the tissue to reduce or eliminate smoke at the surgical site. The invention may be advantageously implemented in an assembly having a surgical pencil for emitting the directed energy stream and liquid mist stream. The liquid mist stream is generated by the surgical pencil, preferably by atomizing a liquid stream supplied thereto (e.g., pressurized via jet atomization). The invention may be utilized in connection with conventional electrosurgical, laser surgery, ultrasound, and other techniques and devices.

51 Claims, 2 Drawing Sheets

DIRECTED ENERGY SURGICAL METHOD AND ASSEMBLY

FIELD OF THE INVENTION

The present invention relates to surgical methods and assemblies employing the application of directed energy to tissue to achieve a predetermined surgical effect, and more particularly, to achieve such effect with reduced attendant smoke at the surgical site.

BACKGROUND OF THE INVENTION

The potential uses and recognized advantages of employing directed energy for surgical purposes are ever-increasing. In particular, for example, electrosurgery and laser surgery techniques are now being widely employed to provide significant localized control advantages in both open and laparoscopic applications relative to prior traditional surgical approaches.

Despite the advantages associated with directed energy surgical techniques, one drawback has been the heating of tissue and attendant generation of smoke. Such smoke impedes observation of the surgical site during surgical procedures, and there is a growing concern that the smoke may be a medium for the transport of pathogens away from the surgical site, including viruses such as HIV. In turn, such concerns have contributed to the use of face shields and masks by surgical personnel.

To date, proposed approaches to deal with smoke have focused upon the utilization of devices to either evacuate the smoke by sucking the same into a filtering system, or alternatively to merely blow the smoke away from the surgical site by a pressurized gas stream. Typical smoke evacuators require the movement of large amounts of air to be effective. As a result, such evacuators tend to be not only noisy but space consuming in a surgical theater where space efficiency is at a premium. Proposed approaches for blowing the smoke away from the surgical site suffer from the fact that, since the smoke is not actually removed, the above-noted concerns are either only partially addressed or otherwise actually compounded.

SUMMARY OF THE INVENTION

Accordingly, the primary objective of the present invention is to provide a surgical method and assembly which employs directed energy to achieve a desired surgical effect while reducing smoke otherwise attendant thereto. Relatedly, it is a further objective to reduce smoke in a manner which does not entail significant space requirements, significant cost, or adverse impact upon the effectiveness of the particular directed energy surgical technique employed.

To achieve the noted objectives, the surgical method of the present invention comprises the step(s) of simultaneously or alternately applying a directed energy stream to a tissue region to achieve a predetermined surgical effect and contacting the predetermined tissue region with a liquid mist stream. As employed herein, the term "liquid mist stream" means a two phase stream of liquid droplets at least partially suspended in a gas.

More particularly, the liquid mist stream employed in the present invention comprises liquid droplets preferably having a diameter of between about 0.1 to 1000 micrometers, and even more preferably between about 0.6 to 60 micrometers. The liquid mist stream is preferably further characterized by providing a mass flow rate at the surgical site of less than about 1511 milligrams/square centimeter per second. Even more preferably, the mass flow rate is less than about 21.5 milligrams/square centimeter per second and greater than about 0.58 milligrams/square centimeter per second.

The liquid mist contacting step preferably includes the step of atomizing a liquid stream to generate the liquid mist stream. Such atomization most preferably is achieved by directing a liquid stream across a pressurized gas stream (i.e., jet atomization). Alternative atomization techniques include emitting a high pressure liquid stream from a nozzle (i.e., pressure atomization), passing a substantially saturated fluid phase stream through a nozzle such that the substantially saturated fluid phase stream undergoes a phase change to a mixed gas and liquid phase stream (i.e., condensation atomization), deflecting a pressurized liquid stream against an angled impact plate (i.e., impact atomization), passing a liquid stream in at least partial contact with a vibrating surface (i.e., vibrating surface atomization), passing a liquid stream through a spinning disk (i.e., spinning disk atomization), passing a high pressure air stream through a thin film water surface (i.e., surface tension atomization), or impacting a plurality of liquid streams (i.e., impact atomization).

The application of a liquid mist stream to tissue heated by the directed energy stream serves to quench tissue pyrolysis, thereby reducing or even eliminating the generation of smoke. Further, it is believed that the liquid droplets in the liquid mist stream serve to reduce any smoke by contacting smoke particles, coalescing therewith, and delivering the same back to the surgical site. Additionally, it is anticipated that another potential benefit of the present invention will be the tissue "washing" achieved by the liquid mist stream, thereby allowing for the identification of bleeders, etc.

While the above-noted benefits are due to the liquid mist stream, it should be appreciated that for a given tissue, the optimal droplet size, droplet velocity, and mass flow rate established should avoid accumulation of excess liquid at the surgical site which may interfere with achieving the desired surgical effect.

The surgical assembly of the present invention preferably comprises a surgical pencil for emitting a directed energy stream and a liquid mist stream, a liquid supply for supplying a liquid (e.g., a sterile irrigation solution commonly used in surgery such as 0.9% NaCl) stream to the surgical pencil, a directed energy source, and control means for selectively controlling the emission of the directed energy stream and/or liquid mist stream. Preferably, the liquid has a density between about 0.7 to 1.8 grams/cubic centimeter. To remove undesired liquid from the surgical site (e.g., body fluid and/or liquid accumulating as a result of the liquid mist stream), the assembly may further include suction means and suction control means either separately provided or supportably interconnected to with the surgical pencil.

The surgical pencil includes a support structure preferably sized for handheld use, a directed energy means for emitting the directed energy stream and a liquid mist generation means for generating the liquid mist stream. The directed energy means and the liquid mist generation means are supportably interconnected to the support structure. By way of primary example, the directed energy source may comprise an electrosurgical generator, a plasma generator, ultrasonic generator, or a surgical laser. If an electrosurgical generator is employed, the directed energy means of the pencil will include a surgical electrode that is electrically interconnected with the generator. In arrangements utilizing a surgical laser, the directed energy means of the surgical pencil may include a laser energy transport means (e.g., optical rod or fiber and a handpiece or similar device to allow the surgeon to direct the laser energy to the tissue).

The liquid mist generation means of the surgical pencil is preferably operatively isolated from the directed energy means, and preferably comprises means for atomizing the liquid stream supplied thereto. Such atomization means may employ jet atomization, pressure atomization, impact atomization, ultrasonic atomization, spinning disk atomization, and surface tension atomization arrangements as indicated above.

In one embodiment of the present invention, the surgical assembly comprises an electrosurgical generator and electrosurgical pencil capable of selectively achieving either a cutting and/or coagulative effective (depending upon the electrical signal provided by the generator), and a jet atomization module interconnected to the pencil. The atomization module includes a first channel interconnected at a first end to a pressurized gas supply so as to provide a pressurized gas stream, a second channel interconnected at a first end to a liquid supply so as to provide a liquid stream and a chamber fluidly interconnected to second ends of both the first and second channels. The second channel is oriented relative to the chamber and first channel so that the liquid stream will cross the pressurized gas stream in the chamber, and the chamber is provided with a reduced outlet end or nozzle for emitting the resultant liquid mist stream about a center axis substantially intersecting with the electrode of the electrosurgical pencil.

The control means may provide for the simultaneous or separate provision of the directed energy stream and the liquid mist stream. In one embodiment of the control means, the control means may comprise one or more switches disposed on the surgical pencil for ready hand control and/or one or more foot pedals, and such control means may be electrically interconnected to either or both the directed energy source and/or the liquid supply and gas supply for the selective control thereof. In another embodiment of the control means, the liquid mist can be generated continuously and the control means can control the directed energy stream. In another embodiment of the control means, the control means can automatically apply mist to the surgical site in response to detecting the application of the directed energy stream to the surgical suite or in response to detecting smoke.

In another embodiment of the control means, the control means senses the tissue temperature at the surgical site and automatically applies the mist to the surgical site while the sensed temperature exceeds a predetermined threshold temperature. In this manner, the control means applies the mist to cool and maintain the tissue temperature within a predetermined range. The predetermined range is preferably defined by a low temperature for which the desired surgical effect is provided and by a high temperature above which tissue pyrolysis and the associated generation of smoke begins to occur.

In still another embodiment of the control means, the control means can automatically alternate at a predetermined frequency between applying the directed energy stream to the surgical site for a predetermined time and applying the liquid mist stream to the surgical site for a predetermined time. By way of primary example, when the directed energy source comprises a surgical laser, due to effects such as absorption and scattering of the laser radiation by the liquid mist stream, it may be preferable for the control means to delay a period of at least about 33 milliseconds, and preferably, no more than about 1 second between the completion of the applying of the liquid mist stream step and the applying the directed energy stream step. In this manner, the directed energy is provided to the tissue to achieve the predetermined surgical effect while also achieving reduced or eliminated smoke at the surgical site.

In the described electrosurgical embodiment, the present invention may offer additional benefits to those generally noted above. For example, the liquid mist stream may prove to enhance the conductivity of the atmosphere in the surgical site, thereby enhancing fulguration control and power delivery efficiencies. Additional embodiments, modifications and advantages will be apparent to those skilled in the art.

DETAILED DESCRIPTION OF THE PREFERRED EMBODIMENT

Figure 1:
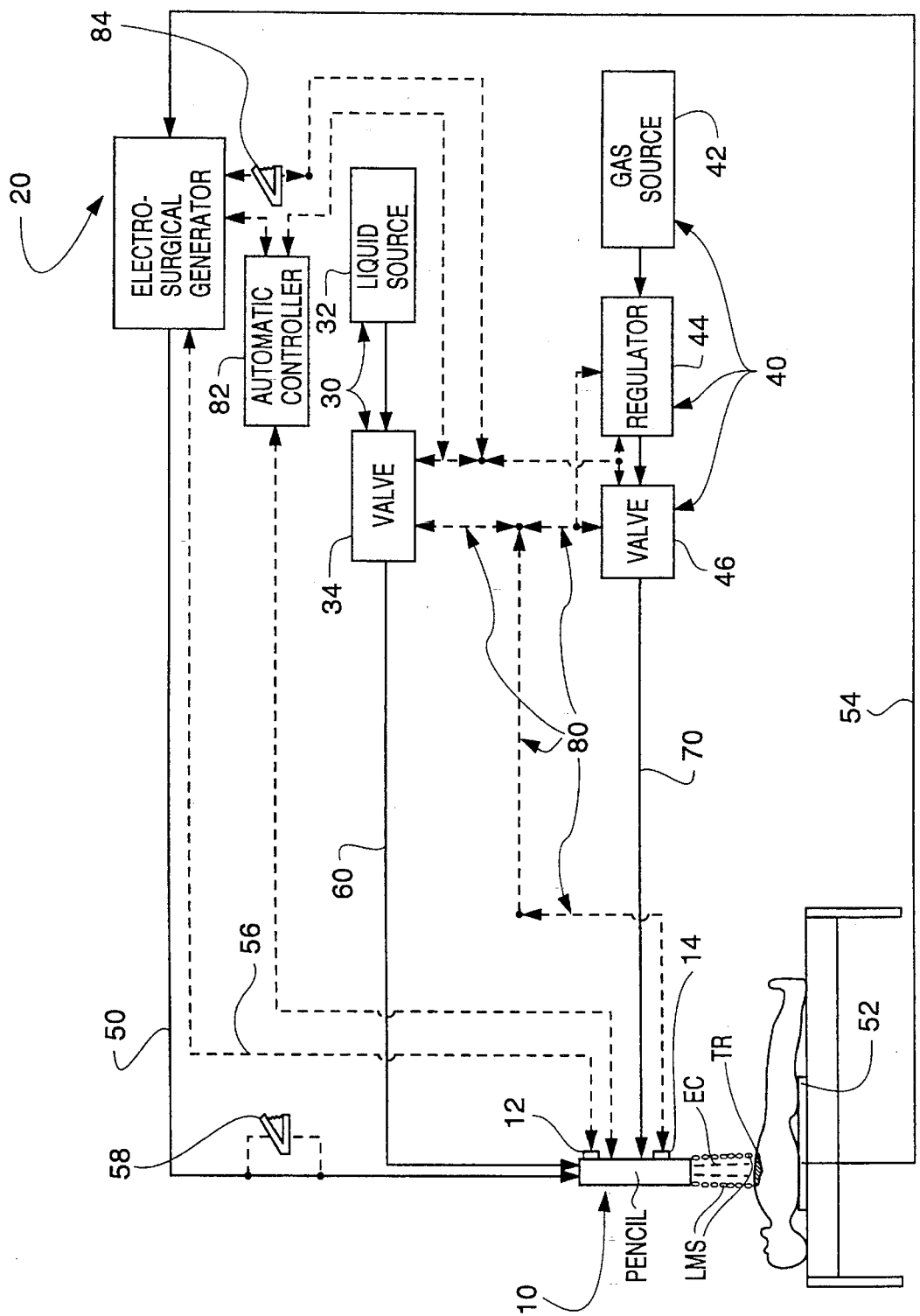
FIG. 1 schematically illustrates one surgical assembly embodiment of the present invention.
Figure 2:
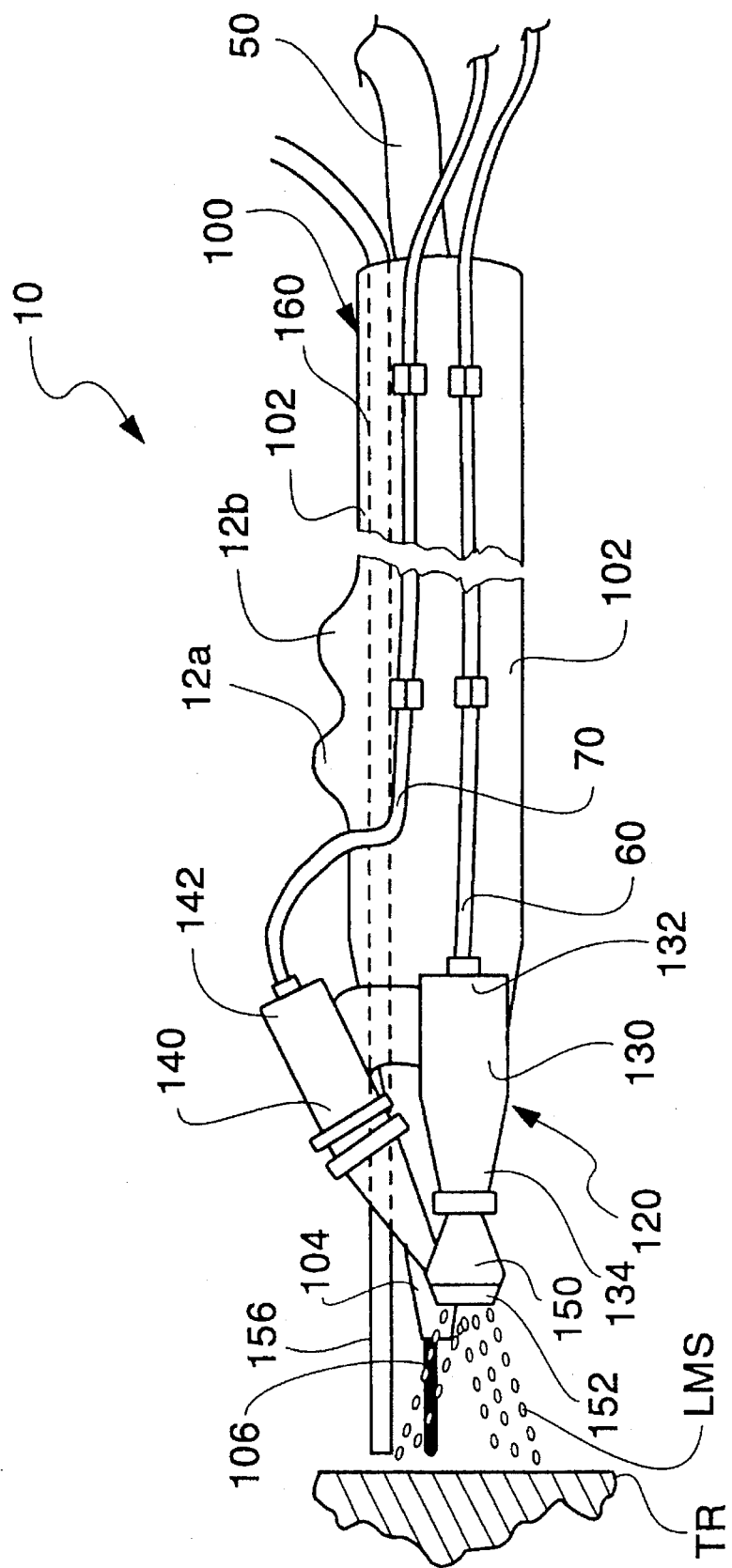
FIG. 2 illustrates one embodiment of a surgical pencil for practicing the present invention.

The surgical assembly embodiment illustrated in FIGS. 1 and 2 includes a surgical pencil 10, and an electrosurgical generator 20, liquid supply 30 and gas supply 40 all operatively interconnected with the surgical pencil 10. Generally, electrical interconnection line 50 delivers an electrical signal from electrosurgical generator 20 to surgical pencil 10 so as to permit surgical pencil 10 to provide an electrical current EC to a tissue region TR, the electrical circuit being completed by pad 52 which is electrically interconnected via electrical interconnection line 54 with electrosurgical generator 20. The liquid supply 30 and gas supply 40 are fluidly connected with surgical pencil 10 via conduits 60 and 70, respectively, so as to permit surgical pencil 10 to supply a liquid mist stream LMS to tissue region TR.

More particularly, liquid supply 30 may comprise a liquid source 32 such as, for example, sterile water, a sterile saline solution, an albumin solution, or a biocompatible surfactant, and a control valve 34 for controlling the flow of a liquid stream to the surgical pencil 10. Gas supply 40 may comprise a gas source 42 such as sterile air, a regulator 44, and a control valve 46 for controlling flow of a gas stream to the surgical pencil 10. The liquid conduit 60 and gas conduit 70 may each be constructed of flexible, plastic tubing material.

Smoke is reduced or eliminated by providing the liquid mist stream LMS to the tissue region TR to maintain the temperature of the tissue region TR within a range for which the desired surgical effect is provided while the generation of smoke is reduced or eliminated. Such control of the liquid mist stream LMS is provided by a control means that can control at least one of the control valves 34 and 46 and the electrical signal from the electrosurgical generator 20. The control means may provide for the simultaneous or separate provision of the directed energy stream and the liquid mist stream LMS.

In one embodiment of the control means, the control means comprises one or more switches disposed on the surgical pencil for ready hand control and/or one or more foot pedals, and such control means is electrically interconnected to both the electrosurgical generator 20 and the liquid source 32 and gas supply 40 for the selective control thereof. As schematically illustrated in FIG. 1, surgical pencil 10 may include electric signal control switch(es) 12 for selectively controlling the supply of the electrical signal from electrosurgical generator 20. In this regard, electric signal control switch(es) 12 may be of a type which allows for the selective provision of a particular electrical signal type (e.g., a cut or coagulation signal) from electrosurgical generator 20. A separate electric control circuit 56 may also be provided between electric signal control switch(es) 12 and electrosurgical generator 20 for the noted control purposes.

Similarly, surgical pencil 10 may include a fluid control switch 14. In this regard, a separate control circuit 80 may be provided between fluid control switch 14 and the valve 34 of liquid supply 30 and the valve 46 and regulator 44 of the gas supply 40 to control both the provision and flow rate of the liquid stream and gas stream, respectively. For operator convenience foot pedal switches 58 and 84 could be utilized for controlling electrosurgical generator 20 and liquid supply 30 and gas supply 40, respectively.

Alternately, more than one liquid supply 40 can be provided with the conduit 60 from each liquid supply 40 being connected to a manifold. The manifold provides selectability between which conduit is fluidly connected to the pencil 10. The fluid control switch 14 can control the manifold to selectively connect one of the liquid supplies to the pencil 10. In this manner, the operator can selectively provide different types of liquid in the liquid mist stream LMS.

In another embodiment of the control means, the provision of the liquid stream and gas stream is controlled via an automatic controller 82 interconnected between the electrosurgical generator 20 and the valve 34 of liquid supply 30 and the valve 46 and regulator 44 of the gas supply 40. The automatic controller 82 automatically applies mist to the surgical site in response to detecting the application of the electrical signal from the electrosurgical generator 20 to the surgical suite.

In another embodiment, the automatic controller 82 can include a sensor for sensing smoke (e.g., ionization sensor) and/or the temperature (e.g., IR temperature sensor) of the tissue region TR. Responsive to the sensor sensing smoke and/or a temperature above a threshold level, the automatic controller 82 can provide the liquid mist stream LMS to cool the tissue region TR and to thereby reduce or eliminate the generation of smoke.

In another embodiment, the automatic controller 82 controls the electrosurgical generator 20 and the control valves 34 and 42 to alternate at a predetermined frequency between applying the electrical signal to the tissue region TR for a first predetermined time and then applying the liquid mist stream LMS to the tissue region TR for a second predetermined time. The ratio of the first and second predetermined times can be adjusted to provide heating of the tissue region TR for the desired surgical effect while reducing or eliminating the generation of smoke. When the directed energy stream is provided by a laser energy source, due to effects such as absorption and scattering of the laser by the liquid mist stream LMS, it may be preferable for the automatic controller 82 to delay a period of at least about 33 milliseconds, and preferably delay no more than about 1 second, between the completion of the applying the liquid mist stream LMS step and the applying the directed energy stream step.

With reference now to FIG. 2, a surgical pencil 10 is illustrated which comprises a conventional electrosurgical pencil 100 and a jet atomization module 120 interconnected thereto. Electrosurgical pencil 100 includes an outer housing 102, an electrode 106 extending from a reduced end 104 of housing 102, and electric signal control switches 12a and 12b for controlling the provision and type of electrical signal (e.g., cut versus coagulation signals) supplied by electrosurgical generator 20. Upon receipt of the electrical signal, electrode 106 emits an electrical current EC to tissue region TR to achieve the desired surgical effect.

Air atomization module 120 includes a gas stream channel 130, a liquid stream channel 140 and an expansion chamber 150 having a nozzle 152 at a front end thereof. The rearward end 142 of the liquid stream channel 140 is fluidly interconnected with conduit 70 that is interconnected to the liquid supply 30. The rearward end 132 of gas stream channel 130 is interconnected via conduit 60 with the gas supply 40. The forward end 134 of gas stream channel 130 is of a reduced diameter and fluidly interconnects with chamber 150 so as to supply the gas stream thereto. The front end of the liquid stream channel 140 is of a reduced diameter and fluidly interconnects with chamber 150 forward of the interconnection between the gas stream channel 130 and chamber 150.

As illustrated, liquid stream channel 140 is oriented at an angle relative to a common center axis for gas stream channel 130 and chamber 150, such that the pressurized gas stream provided by gas stream channel 130 is directed across the liquid stream provided by liquid stream channel 140 within chamber 150 so as to atomize the liquid stream and thereby generate the liquid mist stream LMS. Nozzle 152 at the forward end of chamber 150 serves to define the liquid mist stream pattern and may assist in atomization.

The liquid mist stream LMS comprises liquid droplets preferably having a diameter of between about 0.1 to 1000 micrometers, and even more preferably between about 0.6 to 60 micrometers. The liquid mist stream LMS is preferably further characterized by providing a mass flow rate at the surgical site of less than about 1511 milligrams/square centimeter per second. Preferably, the mass flow rate is less than about 21.5 milligrams/square centimeter per second and greater than about 0.58 milligrams/square centimeter per second.

With continuing reference to FIG. 2, the surgical pencil 10 further includes a suction means comprising a suction nozzle 156 and a suction channel 160. The suction channel 160 fluidly connects the suction nozzle 156 to a conventional vacuum source. The suction nozzle 156 removes undesired fluid buildup via the suction channel 160. The suction means can be controlled by the automatic controller 82 to provide suction during periods when the liquid mist stream LMS is not being provided to the surgical site.

In operation of the surgical pencil 10 illustrated in FIG. 2, an operator may initiate electrosurgical procedures via control of switches 12a, 12b to generate the flow of the electrical current EC from the electrode 106 to the tissue region TR. The flow of the liquid stream and pressurized gas stream from liquid supply 30 and gas supply 40, respectively, may be automatically initiated via the automatic controller 82. Alternatively, the provision of such streams and flow rate thereof may be selectively controlled via the utilization of an optional foot pedal 84. In this regard, the need for and/or density of the liquid mist stream LMS may be less when surgical pencil 10 is being utilized to achieve a coagulative surgical effect than when surgical pencil 10 is being employed for tissue cutting. Further, the selective control over the provision and density of the liquid mist stream LMS reduces the potential need and/or frequency for the utilization of suction means to remove undesired fluid buildup during periods when the smoke is not otherwise being generated in connection with the surgical procedure.

It can be appreciated that the above-noted elements of the disclosed surgical assembly can be provided and utilized as separate elements and the elements can alternately be adapted to be connectable to one another to provide an integrated surgical assembly.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A surgical method for achieving a predetermined surgical effect on tissue while reducing the generation of smoke by quenching tissue pyrolysis comprising:

applying a directed energy stream to a predetermined tissue region to achieve a predetermined surgical effect; and contacting said predetermined tissue region with a liquid mist stream comprising liquid droplets having a diameter of between about 0.1 to 1000 micrometers and a mass flow rate of about 1511 milligrams per square centimeter or less per a 1 second time period to quench tissue pyrolysis.

2. The surgical method of claim 1, said contacting step comprising:

providing said liquid mist stream to said tissue region during at least a portion of said applying step.

3. The surgical method of claim 1, said contacting step comprising:

providing said liquid mist stream to said tissue region responsive to said applying step.

4. The surgical method of claim 1, said contacting step comprising:

detecting smoke; and automatically providing said liquid mist stream to said tissue region responsive to said detecting smoke step.

5. The surgical method of claim 1, said contacting step comprising:

detecting a temperature of said tissue region above a predetermined threshold temperature; and providing said liquid mist stream to said tissue region responsive to said detecting temperature step.

6. The surgical method of claim 1, further comprising a switching step of automatically alternating at a predetermined frequency between said applying step and said contacting step.

7. The surgical method of claim 6, wherein:

said switching step includes the steps of stopping said contacting step, waiting at least about 33 milliseconds, and starting said applying step.

8. The surgical method of claim 6, wherein:

said switching step includes the steps of stopping said contacting step, waiting less than about one second, and starting said applying step.

9. The surgical method of claim 1, wherein said liquid mist stream comprises a biocompatible surfactant.

10. The surgical method of claim 1, wherein said liquid mist stream comprises liquid droplets having a diameter of between about 0.6 to 60 micrometers.

11. The surgical method of claim 1, wherein said contacting step comprises providing a mass flow rate of less than about 21.5 milligrams per square centimeter and more than about 0.58 milligrams per square centimeter to said predetermined tissue region over a 1 second time period.

12. The surgical method of claim 1, said contacting step comprising the step:

atomizing a liquid stream to form said liquid mist stream.

13. The surgical method of claim 12, said atomizing step comprising:

directing said liquid stream across a pressurized gas stream.

14. The surgical method of claim 12, said atomizing step comprising:

passing a substantially saturated fluid phase stream through a nozzle to form a mixed gas and liquid phase stream.

15. The surgical method of claim 12, said atomizing step comprising:

directing said liquid stream through a nozzle.

16. The surgical method of claim 12, said atomizing step comprising:

directing said liquid stream against an angled impact plate.

17. The surgical method of claim 12, said atomizing step comprising:

directing said liquid stream across a vibrating surface.

18. The surgical method of claim 12, said atomizing step comprising:

impacting a plurality of liquid streams.

19. The surgical method of claim 12, said atomizing step comprising:

directing said liquid stream through a spinning disk.

20. The surgical method of claim 12, said atomizing step comprising:

directing a high pressure air stream through said liquid stream.

21. The surgical method as recited in claim 1, wherein said directed energy stream being selected from a group comprising: radiation, electrical current, ultrasonic, and light.

22. The surgical method of claim 1, further comprising a suction step of removing undesired fluid buildup at said predetermined tissue region.

23. The surgical method of claim 22, said suction step being responsive to said contacting step.

24. The surgical method of claim 1, further comprising a selection step of selecting among a plurality of liquid sources for communication to said contacting step.

25. A surgical assembly for achieving a predetermined surgical effect on tissue while reducing the generation of smoke by quenching tissue pyrolysis, comprising:

directed energy means for applying a directed energy stream to a predetermined tissue region;

a liquid mist means for generating a liquid mist stream comprising liquid droplets having a diameter of between about 0.1 to 1000 micrometers and a mass flow rate of about 1511 milligrams per square centimeter or less per 1 second time period for contact with said tissue region; and a surgical pencil housing sized for handheld use, wherein said directed energy means and said liquid mist means are supportably connected to said surgical pencil housing and said liquid mist means is separate from and offset from said directed energy means.

26. A surgical assembly as recited in claim 25, wherein said directed energy means and said liquid mist means are supportably connectable to said surgical pencil housing.

27. A surgical assembly as recited in claim 25, further comprising:

control means for activating one of said directed energy means and said liquid mist means.

28. A surgical assembly as recited in claim 27, wherein:

said control means activates said liquid mist means to generate said liquid mist stream at least partially contemporaneously with said directed energy means applying said directed energy stream.

29. A surgical assembly as recited in claim 27, wherein:

said control means comprises a smoke sensor for detecting smoke at said predetermined tissue region, said control means activates said liquid mist means to generate said liquid mist stream responsive to said smoke sensor sensing smoke.

30. A surgical assembly as recited in claim 27, wherein:

said control means comprises a temperature sensor for detecting a temperature of said predetermined tissue region, said control means activates said liquid mist means to generate said liquid mist stream responsive to said temperature sensor sensing a temperature above a predetermined threshold temperature.

31. A surgical assembly as recited in claim 27, wherein:

said control means automatically alternates at a predetermined frequency between activating said directed energy means and then said liquid mist means.

32. A surgical assembly as recited in claim 31, wherein:

said control means waits at least 33 milliseconds between stopping said liquid mist means and activating said directed energy means.

33. A surgical assembly as recited in claim 31, wherein:

said control means waits less than about 1 second between stopping said liquid mist means and activating said directed energy means.

34. A surgical assembly as recited in claim 25, wherein:

said liquid mist means comprises a plurality of liquid sources, a manifold, and a nozzle;

each of said plurality of liquid sources fluidly connected to said manifold;

said manifold fluidly connected to said nozzle; p1 control means for regulating said manifold to connect one of said plurality of liquid sources to said nozzle.

35. A surgical assembly as recited in claim 25, further comprising:

a directed energy supply operatively interconnected to said directed energy means; and a liquid supply for supply of a liquid stream to said liquid mist means.

36. A surgical assembly as recited in claim 35, further comprising:

suction means for removing undesired fluid buildup from said predetermined tissue region, said suction means supportably connectable to said surgical pencil housing.

37. A surgical assembly as recited in claim 25, wherein said directed energy means comprises:

electrosurgical generator, a plasma generator, ultrasonic generator, or a surgical laser.

38. A surgical assembly as recited in claim 25, wherein:

said liquid mist means generates a liquid mist stream having a biocompatible surfactant.

39. A surgical assembly as recited in claim 25, wherein:

said liquid mist means generates a liquid mist stream comprising liquid droplets having a diameter of between about 0.6 to 60 micrometers.

40. A surgical assembly as recited in claim 25, wherein:

said liquid mist means provides a mass flow rate to said predetermined tissue region of less than about 21.5 milligrams per square centimeter and more than about 0.58 milligrams per square centimeter over a 1 second time period.

41. A surgical assembly as recited in claim 25, wherein:

said liquid mist means comprises an atomizer.

42. A surgical assembly as recited in claim 25, wherein:

said liquid mist means comprises a jet atomizer.

43. A surgical assembly as recited in claim 25, wherein:

said liquid mist means comprises a condensation atomizer.

44. A surgical assembly as recited in claim 25, wherein:

said liquid mist means comprises a pressure atomizer.

45. A surgical assembly as recited in claim 25, wherein:

said liquid mist means comprises an impact atomizer.

46. A surgical assembly as recited in claim 25, wherein:

said liquid mist means comprises an vibrating surface atomizer.

47. A surgical assembly as recited in claim 25, wherein:

said liquid mist means comprises a spinning disk atomizer.

48. A surgical assembly as recited in claim 25, wherein:

said liquid mist means comprises a surface tension atomizer.

49. A surgical assembly as recited in claim 25, wherein:

said liquid mist means comprises an impact atomizer.

50. A surgical method for achieving a predetermined surgical effect on tissue while reducing the generation of smoke by quenching tissue pyrolysis, comprising:

applying directed light from a surgical laser to a predetermined tissue region to achieve a predetermined surgical effect;

contacting said predetermined tissue region with a liquid mist stream; and waiting for at least a predetermined time period between stopping said contacting step and starting said applying step.

51. The surgical method of claim 50, further comprising a switching step of alternating at a predetermined frequency between said applying step and said contacting step.

* * * * *